(12) United States Patent
Valenta et al.

(10) Patent No.: US 7,696,314 B2
(45) Date of Patent: Apr. 13, 2010

(54) HYPOALLERGENIC MUTANT POLYPEPTIDES BASED ON FISH PARVALBUMIN

(75) Inventors: Rudolf Valenta, Theresienfeld (AT); Peter Valent, Vienna (AT); Susanne Spitzauer, Vienna (AT); Ines Swoboda, Vienna (AT)

(73) Assignee: Biomay Produktions- und Handelsaktiengesellschaft, Vienna (AT)

( * ) Notice: Subject to any disclaimer, the term of this patent is extended or adjusted under 35 U.S.C. 154(b) by 89 days.

(21) Appl. No.: 10/924,200

(22) Filed: Aug. 24, 2004

(65) Prior Publication Data
US 2006/0140969 A1    Jun. 29, 2006

(30) Foreign Application Priority Data
Sep. 4, 2003  (EP) .................................. 03020063

(51) Int. Cl.
C07K 14/00    (2006.01)
A61K 38/00    (2006.01)
(52) U.S. Cl. ....................... 530/350; 530/300
(58) Field of Classification Search ........................ None
See application file for complete search history.

(56) References Cited

OTHER PUBLICATIONS

Swain et al. (1989, J. Biol. Chem., vol. 264, p. 16620-16628).*
Troxler et al. (1999, Analytical Biochemistry, vol. 268, p. 64-71).*
Bugajska-Schretter et al. (2000, Gut, vol. 46, p. 661-669).*
Swoboda et al. (May 1, 2002, J. Immunol., vol. 168, p. 4576-4584).*
Rhyner et al. (1996, Biochimica et Biophysica Acta, vol. 1313, p. 179-186).*
Miranda et al. (1999, Proc. Natl. Acad. Sci., vol. 96, p. 1181-1186).*
Ohki et al. (1986) The Journal of Biological Chemistry, vol. 261, pp. 1778-1781.*
Lottor et al., Identification of an Epitope on the Entamoeba histolytica 170-kD Lectin Conferring Antibody-mediated Protection against Invasive Amebiasis., J. Exp. Med., 1997, vol. 185, pp. 1793-1801.*
Vrtala, Suzanne et al.; Conversion of the Major Birch Pollen Allergen, Bet v 1, into Two Nonanaphylactic T Cell Epitope-containing Fragments; J. Clin. Invest., vol. 99, No. 7, Apr. 1977, 1673-1681; The American Society for Clinical Investigation, Inc., Ann Arbor, MI, USA.
Westritschnig, Kerstin et al., Generation of an Allergy Vaccine by Disruption of the Three-Dimensional Structure of the Cross-Reactive Calcium-Binding Allergen, Phl p 7[1]; The Journal of Immunology, 2004, 172:5684-5692; The American Association of Immunologists, Inc., Bethesda, MD, USA.

* cited by examiner

Primary Examiner—David J Steadman
Assistant Examiner—Alexander D Kim

(57) ABSTRACT

The present invention relates to non-naturally occurring polypeptides derived from fish allergens such as parvalbumin Cyp c 1.01 from carp. The polypeptides display reduced allergenic activity and are useful as allergy vaccines for treatment of sensitized allergic patients and for prophylactic vaccination.

4 Claims, 7 Drawing Sheets

Figure 6

Figure 1:
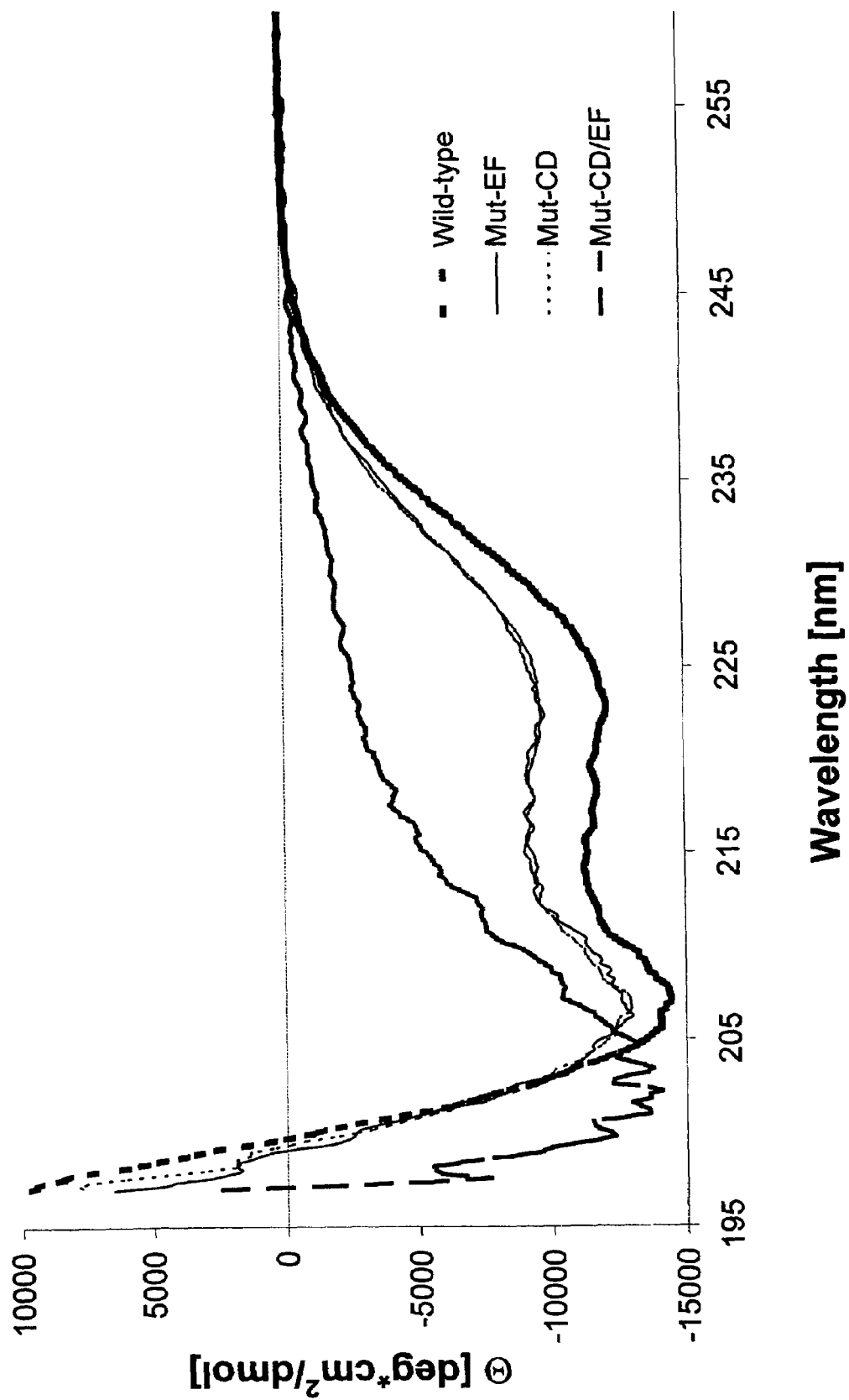

```
Cyp c 1.01   1 MAFAGILNDADITAALQGCQAADSFDYKSFFAKVGLSAKTPDDIKKAFAVIDQDKSGFIE 60
               MAFAG LNDADITAAL  C A  SF  KSFF KVGL  K  DD KKAFA IDQDKSGFIE
Ict.punct.  17 MAFAGVLNDADITAALDACKADGSFNHKSFFTKVGLTGKSADDVKKAFAIIDQDKSGFIE 76

Cyp c 1.01  61 EDELKLFLQNFSAGARALTDAETKAFLKAGDSDGDGKIGVDEFAALVKA 109
               EDELKLFLQNF  ARALTDAETK FLKAGD DGDGKIGVDEFA LVKA
Ict.punct.  77 EDELKLFLQNFKSSARALTDAETKTFLKAGDTDGDGKIGVDEFASLVKA 125
```

HYPOALLERGENIC MUTANT POLYPEPTIDES BASED ON FISH PARVALBUMIN

The present invention relates to polypeptides derived from the major fish allergen carp parvalbumin. The polypeptides display reduced allergenic activity and are useful as allergy vaccines for treatment of sensitized allergic patients and for prophylactic vaccination.

Together with milk, egg, peanuts, tree nuts and shellfish, fish represents the most important source of allergens in the induction of IgE mediated food hypersensitivity (Bischoff et al., 1996; Etesamifar and Wüthrich 1998; Sampson 1999). Although not a common health problem on a world wide basis, fish allergy can reach a prevalence of 1 per 1000 individuals in fish-eating and fish-processing countries (Aas 1987). In sensitised individuals contact with and consumption of fish, but also inhalation of vapour generated during cooking can cause a variety of IgE-mediated clinical symptoms affecting the skin, the respiratory tract and the gastrointestinal tract (Aas 1987; Pascual et al., 1992; O'Neil et al., 1993).

Paravalbumins, small calcium-binding proteins, highly abundant in the white muscles of lower vertebrates (Pechere 1997) and present in lower amounts in fast twitch muscles of higher vertebrates (Lehky et al., 1974), were identified as the major fish allergens. These proteins belong to the EF-hand superfamily of calcium-binding proteins, which is characterised by the presence of helix-loop-helix metal-binding domains, termed EF-hands (Kretsinger, 1980). Parvalbumins contain three such EF-hand motifs, (AB, CD and EF sites) (Berchtold, 1989; Heizmann and Hunziker, 1991; Ikura, 1996). Two of the sites (CD and EF) are paired to form a stable domain capable of binding two cations, $Ca^{2+}$ or $Mg^{2+}$. The first site (AB) is unable to bind cations, but forms a cap that covers the hydrophobic surface of the pair of functional domains and thereby acts as a stabilising element (Kretsinger and Nockold, 1973; Declercq et al., 1991; Permyakov et al., 1991). Based on amino acid sequence data the parvalbumin protein family can be subdivided into two evolutionary distinct lineages: the α group, consisting of less acidic parvalbumins with isoelectric points at or above pI 5.0 and the β group, consisting of more acidic parvalbumins with isoelectric points at or below pI 4.5 (Goodman and Pechere, 1977).

Parvalbumins show a remarkable resistance to heat, denaturing chemicals and proteolytic enzymes, characteristics, which might enable them to act as potent sensitising agents for more than 95% of fish allergic patients (Aas and Elsayed, 1969; De Martino et al., 1990; O'Neil et al., 1993; Lindstroem et al., 1996; Bugajska-Schretter et al., 1998).

The inventors found that patients who mount IgE antibodies against parvalbumin of one fish species also recognise the homologous proteins from other fish species (Bugajska-Schretter et al., 1998). In IgE competition experiments performed with purified carp parvalbumin they further showed that carp parvalbumin contains the majority of IgE epitopes present in fish protein extracts of various species (Bugajska-Schretter et al., 2000). This demonstrated the importance of parvalbumins as cross-reactive fish allergens and explained why allergic individuals exhibit clinical symptoms upon contact with various fish species.

Until now, the only curative approach towards type I allergy is allergen-specific immunotherapy, which is based on the systemic administration of increasing amounts of disease-eliciting allergens in the form of allergen-containing extracts, with the aim to induce a state of allergen-specific non-responsiveness in the patient (Bousquet et al., 1998). However, although allergen-specific immunotherapy is most widely used for the treatment of respiratory- and venom allergies, it is too dangerous to be applied in case of food allergies. This is due to the extremely high risk of severe anaphylactic reactions caused by systemic application of food allergens and by the presence of several ill defined components in food extracts (and especially in fish extracts).

During the last few years the application of recombinant DNA technology into the field of Allergology has allowed to produce an increasing number of biologically active recombinant allergens by cDNA cloning and expression in heterologous hosts (Valenta and Kraft, 1995). With recombinant allergens, which closely mimic the allergenic activity of their natural counterparts, it has become possible to determine the individual patients reactivity profile and to develop component-based vaccination strategies for patient-tailored specific immunotherapy (Valenta et al., 1998).

By screening of a carp muscle cDNA expression library with serum IgE of fish allergic patients the inventors isolated cDNA clones coding for IgE-reactive parvalbumin isoforms (Cyp c 1.01 and Cyp c 1.02) and produced the first recombinant fish parvalbumin (rCyp c 1.01) with immunological features comparable to the natural allergen (Swoboda et al., 2002). rCyp c 1.01 reacted with IgE from all fish allergic patients tested, induced specific and dose-dependent basophil histamine release and contained most of the IgE epitopes (70%) present in natural allergen extracts from various fish species.

The wildtype rCyp c 1.01 molecule can not be used for therapeutical purposes. Administration, even at very low doses, would carry an enormous risk of inducing life-threatening anaphylactic side effects. Objective of the present invention is to provide mutants or variants of rCyp c 1.01 with reduced allergenic activity. The inventors propose that one possibility to obtain such hypoallergenic parvalbumin derivatives will be the site-directed mutagenesis of critical amino acids either within or outside of IgE epitopes in a way that alters the fold and decreases the secondary structure content of the protein. However, the resistance of parvalbumins to destabilising factors such as heat, denaturing chemicals or proteolytic enzymes (Elsayed and Aas, 1971) suggests that it might be difficult to obtain dramatic conformational changes, which modify the allergenic activity of the molecule, by alteration of only a few amino acids.

The invention aims at providing means for the prophylactic or therapeutic treatment of food allergy to fish allergens. It has been found that mutants of carp parvalbumin, e.g., of Cyp c 1.01, show strongly reduced IgE binding and are thus useful as hypoallergenic agents. The amino acid sequence of Cyp c 1.01 is shown in SEQ ID NO:1. The invention relates to a non-naturally occurring or mutated polypeptide derived from fish parvalbumin, selected from the group consisting of (a) polypeptides comprising an amino acid sequence in which in respect to the amino acid sequence as shown in SEQ ID NO:1 one to 15 amino acid residues are deleted, substituted and/or added;

(b) polypeptides comprising a fragment of (a), wherein the fragment has a length of at least 15 amino acids and at least 90% of the amino acid residues of the fragment are identical to corresponding residues of the amino acid sequence as shown in SEQ ID NO:1;

(c) polypeptides comprising a fragment of the amino acid sequence as shown in SEQ ID NO:1, wherein the fragment has a length of at least 15 amino acids;

(d) polypeptides consisting of a fragment of (a), wherein the fragment has a length of at least 10 amino acids and at least 80% of the amino acid residues of the fragment are identical to corresponding residues of the amino acid sequence as shown in SEQ ID NO:1; and (e) polypeptides consisting of a fragment of the amino acid sequence as shown in SEQ ID NO:1, wherein the fragment has a length of at least 10 amino acids.

As used herein, the term "polypeptide" denotes a compound comprising at least 7 amino acids which are linked by peptide bonds. The polypeptide is preferably composed only of amino acids, but it may also comprise non-proteinaceous components. The length of the polypeptide is preferably at least 10 amino acids, more preferably at least 15 amino acids. The polypeptide may also be a fusion protein comprising a portion which is derived from Cyp c 1.01 and a fusion partner. The portion derived from Cyp c 1.01 may further be linked to a carrier molecule, e.g. keyhole limpet hemocyanin (KLH).

The term "fish parvalbumin" as used herein designates a calcium binding polypeptide, the amino acid sequence of which is at least 60% identical to the amino acid sequence as shown in SEQ ID NO:1. These polypeptides have amino acid sequences identical to the respective naturally occurring fish allergens.

A "mutated" polypeptide according to the invention is a polypeptide which has been manipulated by introducing a mutation (substitution, addition or deletion) to a naturally occurring polypeptide such as a wild type fish parvalbumin.

A "non-naturally occurring" polypeptide according to the invention is a polypeptide which is structurally different from polypeptides that can be found in nature such as wild type fish parvalbumins.

An amino acid substitution denotes the replacement of one amino acid with a different amino acid. Preferably, acidic residues (glutamic acid, aspartic acid) are substituted. The substituting amino acid may be of any type, preferably it is not an acidic amino acid, more preferably it is a hydrophobic amino acid, still more preferably the substituting amino acid is selected from the group consisting of glycine, alanine, valine, isoleucine and leucine, most preferably, it is alanine.

In one embodiment, the polypeptide of the invention comprises an amino acid sequence which has 1 to 15 amino acid deletions, substitutions and/or additions in respect to the amino acid sequence as shown in SEQ ID NO:1. Preferably, the number of amino acid deletions, substitutions and/or additions is 1 to 10, more preferably 1 to 6, still more preferably 2 to 6, most preferably 2 to 4, e.g., about 4. The polypeptides of this embodiment are at least about 94 amino acids in length, the preferred length is about 109 amino acids. The preferred polypeptides have 1, 2, 3, 4, 5 or 6 amino acid substitutions in respect to the amino acid sequence as shown in SEQ ID NO:1.

The one or more amino acid substitutions may include substitutions at amino acid positions 52, 54, 91 and/or 93 of SEQ ID NO:1. The polypeptide of the invention may comprise an amino acid sequence which has at least one amino acid substitution in respect to the amino acid sequence as shown in SEQ ID NO:1 wherein said at least one amino acid substitution is at a position of SEQ ID NO:1 selected from amino acid positions 52, 54, 91 or 93 of SEQ ID NO:1. The polypeptide of the invention may comprise an amino acid sequence which has at least two amino acid substitutions in respect to the amino acid sequence as shown in SEQ ID NO:1 wherein said at least two amino acid substitutions are at positions of SEQ ID NO:1 selected from amino acid positions 52, 54, 91 or 93 of SEQ ID NO:1. The polypeptide of the invention may comprise an amino acid sequence which has at least three amino acid substitutions in respect to the amino acid sequence as shown in SEQ ID NO:1 wherein said at least three amino acid substitutions are at positions of SEQ ID NO:1 selected from amino acid positions 52, 54, 91 or 93 of SEQ ID NO:1. The polypeptide of the invention may comprise an amino acid sequence which has at least four amino acid substitutions in respect to the amino acid sequence as shown in SEQ ID NO:1 wherein said at least four amino acid substitutions are at positions of SEQ ID NO:1 selected from amino acid positions 52, 54, 91 or 93 of SEQ ID NO:1.

The most preferred polypeptides of this aspect comprise an amino acid sequence as shown in SEQ ID NO:2, SEQ ID NO:3 or SEQ ID NO:4. The polypeptide represented by SEQ ID NO:2 carries two mutations as compared with the amino acid sequence as shown in SEQ ID NO:1, namely D52A and D54A. The polypeptide represented by SEQ ID NO:3 has the mutations D91A and D93A as compared with SEQ ID NO:1. The polypeptide represented by SEQ ID NO:4 carries mutations D52A, D54A, D91A and D93A as compared with SEQ ID NO:1. Further aspects of the invention are polypeptides comprising amino acids 52 to 93, 52 to 102, 40 to 102, 30 to 105, 20 to 105, 10 to 109 or 2 to 109 of SEQ ID NO:4. The respective lower and upper limits may be cross-combined. These amino acid positions can be applied to other fish parvalbumins as well (see infra).

The invention further concerns polypeptides comprising a fragment of the polypeptides described above (a). The fragment has a length of at least 15 amino acids, i.e. it consists of at least 15 consecutive amino acids of the polypeptide described above (a). Preferably, the length of the fragment is at least 20 amino acids, more preferably at least 25 amino acids, even more preferably at least 30 amino acids. At least 90% of the amino acid residues of the fragment are identical to corresponding residues of the amino acid sequence as shown in SEQ ID NO:1, preferably at least 92%, most preferably at least 95%. Percent sequence identity is determined by conventional methods. The degree of identity of the amino acid sequence of the fragment to SEQ ID NO:1 may be determined by comparing the amino acid sequence of the fragment and SEQ ID NO:1 using the program "Blast 2 sequences" (Tatusova et al. (1999) FEMS Microbiol. Lett. 174, 247-250). The parameters which are used in this context are: matrix: BLOSUM 62; gap open: 11; gap extension: 1; X drop off: 50; expect: 10; word size: 3; filter: no.

In another embodiment, the polypeptide of the invention comprises a fragment of the amino acid sequence as shown in SEQ ID NO:1 with a length of at least 15 amino acids. The fragment consists of at least 15 consecutive amino acids of the amino acid sequence as shown in SEQ ID NO:1, preferably at least 20 consecutive amino acids, more preferably at least 25 consecutive amino acids, most preferably at least 30 consecutive amino acids.

The polypeptides of the invention may essentially consist of a fragment of the polypeptides described above (a). This fragment essentially consists of at least 10 consecutive amino acids of the polypeptide described above (a), preferably at least 15 consecutive amino acids, more preferably at least 20 consecutive amino acids, even more preferably at least 25 consecutive amino acids, most preferably at least 30 consecutive amino acids. The amino acid sequence of the fragment is at least 80% identical to corresponding residues of the amino acid sequence as shown in SEQ ID NO:1. The degree of amino acid sequence identity is determined as described supra. The sequence identity of the fragments to the amino acid sequence of SEQ ID NO:1 is preferably at least 85%, more preferably at least 90%, most preferably at least 95%.

In another embodiment, the polypeptide of the invention consists of a fragment of the amino acid sequence as shown in SEQ ID NO:1. This fragment consists of at least 10 consecutive amino acids of the amino acid sequence as shown in SEQ ID NO:1, preferably at least 15 consecutive amino acids, more preferably at least 20 consecutive amino acids, even more preferably 25 consecutive amino acids, most preferably at least 30 consecutive amino acids. Preferred polypeptides comprise at least the amino acids forming one of the EF hand motifs (amino acids D52-E63 or D91-E102 of the amino acid sequence as shown in SEQ ID NO:1). Examples are the polypeptides consisting substantially of the amino acid sequence as shown in SEQ ID NO:5 (first EF hand motif) or SEQ ID NO:6 (second EF hand motif, respectively, optionally coupled to a carrier molecule such as keyhole limpet hemocyanin (KLH).

The polypeptides of the present invention usually have reduced allergenic activity compared to wild type Cyp c 1.01. According to the invention the term "allergenic activity" denotes the capability of a compound or composition to induce an allergic reaction in a sensitized mammal, e.g. in a fish allergic patient. An allergic reaction may be mast cell degranulation, positive skin reaction and/or nasal reaction. The allergenic activity is preferably defined in suitable in vitro or in vivo tests. The allergenic activity may be determined in a skin test as described in van Hage-Hamsten et al. J. Allergy Clin. Immunol. 1999, 104, pp. 969-977 or in Pauli et al. Clin. Exp. Allergy 2000, 30, pp. 1076-1084. The allergenic activity of wild type Cyp c 1.01 may be determined using recombinantly produced Cyp c 1.01 essentially consisting of the amino acid sequence as shown in SEQ ID NO:1.

Preferably the allergenic activity of the polypeptide is less than 50% of the allergenic activity of the wild type Cyp c 1.01. More preferably the allergenic activity of the polypeptide is less than 25% of the wild type protein. In the most preferred embodiment the polypeptide has substantially no allergenic activity. Generally, the histamine release induced by the polypeptide of the invention is significantly reduced compared to the histamine release induced by Cyp c 1.01. A preferred in vitro test for determining the histamine release is the basophil histamine release assay as described in Vrtala et al., J. Clin. Invest. 1997, 99, pp. 1673-1681. Preferably, the histamine release is reduced by at least 25%, more preferably by at least 50%, most preferably by at least 75%, determined at that concentration of allergen at which Cyp c 1.01 shows maximum histamine release.

The allergenic activity referred to above may vary depending on the serum or patient examined the values given above refer to the average allergenic activity, e.g. determined through examination of at least 20 randomly selected fish allergic patients or their sera.

The polypeptides of the invention usually show reduced binding to IgE antibodies from fish allergic patients compared with wild type Cyp c 1.01 (SEQ ID NO:1). The IgE binding activity is preferably reduced by at least 25%, more preferably by at least 50%, most preferably by at least 75%. Recombinant Cyp c 1.01 essentially consisting of the amino acid sequence as shown in SEQ ID NO:1 can be used to determine the IgE binding activity of wild type Cyp c 1.01. IgE binding of polypeptides may be determined in an ELISA or by Western blot analysis or dot blot experiments using serum from a fish allergic patient. Fish allergy is diagnosed according to a case history indicative for fish allergy, positive skin test reaction to fish allergens and/or the detection of specific IgE antibodies to fish allergens in serum. Dot blots can be quantified by measuring the amount of $^{125}$I-labeled anti-human IgE antibodies by gamma counting as described (Niederberger et al. J. Allergy Clin. Immunol. 1998, 102, 579-591).

The IgE binding activity referred to above may vary depending on the serum or patient examined. the values given above refer to the average IgE binding activity, e.g. determined through examination of at least 20 randomly selected fish allergic patients or their sera (see table 3).

In some cases, a given polypeptide of the invention may show reduced binding activity to IgE antibodies of some fish allergic patients, whereas it shows unaltered or even increased binding to IgE antibodies of other fish allergic patients. Such polypeptides are also within the scope of the invention, since they are useful in the treatment of patients from which the IgE antibodies with reduced binding were obtained.

The invention further relates to a method for the treatment of a fish allergic patient, comprising (a) determining the binding activity of a polypeptide of the invention to IgE antibodies from the serum of said patient; (b) determining the binding activity of Cyp c 1.01 to the said IgE antibodies; and (c) treating the patient with the polypeptide of the invention if the IgE binding activity determined in (a) is significantly lower than the IgE binding activity determined in (b). Preferably, the IgE binding activity determined in (a) is less than 75%, preferably less than 50%, more preferably less than 25%, most preferably less than 10% of that determined in (b).

The invention further relates to a method for making a medicament for the treatment of a fish allergic patient, comprising (a) determining in vitro the binding activity of a polypeptide of the invention to IgE antibodies from the serum of said patient; (b) determining in vitro the binding activity of Cyp c 1.01 to the said IgE antibodies; and (c) selecting the polypeptide of the invention and mixing it with a pharmaceutically acceptable carrier or diluent if the IgE binding activity determined in (a) is significantly lower than the IgE binding activity determined in (b). Preferably, the IgE binding activity determined in (a) is less than 75%, preferably less than 50%, more preferably less than 25%, most preferably less than 10% of that determined in (b).

Preferably, the fish parvalbumin-derived polypeptides of the invention induce IgG antibody responses in vivo. Therefore, the polypeptides described above generally comprise at least one IgG epitope. A polypeptide comprises at least one IgG epitope when it is capable of eliciting an IgG antibody response in an individual or a test animal. A corresponding test for determining an IgG response is described in European Patent Application No. 02021837 relating to hypoallergenic polypeptides based on pollen allergens. More preferably, these IgG antibodies are "blocking antibodies" or "protective antibodies" which prevent IgE antibodies from binding to Cyp c 1.01. A significant reduction of allergic symptoms may be achieved in this way.

The invention further relates to a hybrid polypeptide essentially consisting of 2 or 3 fragments of different fish parvalbumins and/or of different polypeptides described above. The hybrid polypeptide preferably has a length of at least 90 amino acids.

It has been found that the polypeptides of the invention which carry mutations corresponding to the mutations represented by amino acid sequences SEQ ID NO:2, SEQ ID NO:3, SEQ ID NO:4, SEQ ID NO:5 or SEQ ID NO:6 have unexpected advantageous properties. The amino acid positions targeted in these amino acid sequences can be substituted or deleted in other fish parvalbumins as well. Therefore, the present invention relates to a mutated polypeptide derived from a fish parvalbumin, wherein in respect to the wild type sequence of the fish parvalbumin amino acid positions have been substituted or deleted which correspond to the amino acid residues which are substituted or deleted in respect to SEQ ID NO:1 in SEQ ID NO:2, SEQ ID NO:3, SEQ ID NO:4, SEQ ID NO:5 or SEQ ID NO:6. The identification of amino acid positions in other fish parvalbumins which correspond to the amino acid positions mutated in anyone of SEQ ID NO:2 to 6 is within the level of ordinary skill. For example, the skilled person may align anyone of the sequences as shown in SEQ ID NO:1 to 6 with the amino acid sequence of a given fish parvalbumin using the program "Blast 2 sequences" described above. From the alignment the corresponding amino acid positions to be mutated can easily be derived. As an example, FIG. 6 shows an alignment of Cyp c 1.01 parvalbumin and parvalbumin from *Ictalurus punctatus* (SEQ ID NO:10). The amino acid positions to be substituted or deleted correspond to D52, D54, D91 and/or D93 of SEQ ID NO:1. These positions correspond to D68, D70, D107 and D109 of the amino acid sequence of parvalbumin from *Ictalurus punctatus* (SEQ ID NO:10). The polypeptides derived from fish parvalbumins may be comprised in a larger polypeptide or be coupled to a suitable carrier protein such as KLH. They may also have reduced allergenic activity and IgE binding capacity compared with their respective wild type forms and are capable of inducing an IgG response as described supra. The amino acid sequences of several fish parvalbumins are known:

TABLE 1

| Definition | accession No. | organism | SEQ ID NO: |
|---|---|---|---|
| parvalbumin isoform 1b | AAO33403 | *Danio rerio* | 7 |
| Parvalbumin alpha (A1) | P09227 | *Cyprinus carpio* | 8 |
| Cyp c 1.02 | CAC83659 | *Cyprinus carpio* | 9 |
| parvalbumin | AAO25757 | *Ictalurus punctatus* | 10 |
| Gad m 1 | Q90YK9 | *Gadus morhua* | 11 |
| parvalbumin | NP_571591 | *Danio rerio* | 12 |
| parvalbumin isoform 1c | AAO33402 | *Danio rerio* | 13 |
| parvalbumin I | 1206380A | *Electrophorus* sp. | 14 |
| Sco j 1 | P59747 | *Scomber japonicus* | 15 |

Polypeptides derived from fish parvalbumins other than Cyp c 1.01 preferably comprise substitutions or deletions at amino acid positions corresponding to those substituted in any one of SEQ ID NO:2 to 6.

The invention pertains to a non-naturally occurring polypeptide derived from a wild type fish parvalbumin, comprising an amino acid sequence in which in respect to the amino acid of said wild type fish parvalbumin the amino acids at the positions corresponding to positions 52 and 54 of SEQ ID NO:1 are substituted.

The invention further relates to a non-naturally occurring polypeptide derived from a wild type fish parvalbumin, comprising an amino acid sequence in which in respect to the amino acid of said wild type fish parvalbumin the amino acids at the positions corresponding to positions 91 and 93 of SEQ ID NO:1 are substituted.

The invention further relates to a non-naturally occurring polypeptide derived from a wild type fish parvalbumin, comprising an amino acid sequence in which in respect to the amino acid of said wild type fish parvalbumin the amino acids at the positions corresponding to positions 52, 54, 91 and 93 of SEQ ID NO:1 are substituted.

An example is a non-naturally occurring polypeptide derived from *Danio rerio* parvalbumin isoform 1b, comprising an amino acid sequence in which in respect to the amino acid sequence as shown in SEQ ID NO:7 the amino acids at positions 52 and 54; or at positions 91 and 93; or preferably at positions 52, 54, 91 and 93 are substituted. Another example is a non-naturally occurring polypeptide derived from *Cyprinus carpio* parvalbumin alpha (A1), comprising an amino acid sequence in which in respect to the amino acid sequence as shown in SEQ ID NO:8 the amino acids at positions 51 and 53; or at positions 90 and 92; or preferably at positions 51, 53, 90 and 92 are substituted.

Wild type Cyp c 1.01 represented by the amino acid sequence as shown in SEQ ID NO:1 and proteins essentially consisting of wild type Cyp c 1.01 are not polypeptides of the present invention. Naturally occurring fish parvalbumins or recombinant proteins consisting of the same amino acids are not polypeptides of this application (e.g. the parvalbumins listed in table 1 above, etc.).

Hypoallergenic parvalbumins do not necessarily consist only of amino acid sequences derived from parvalbumin proteins. It is possible that they also comprise 'tag' sequences which will facilitate the purification of the proteins after expression in the host cells. An example for such a 'tag' is the hexahistidine tag which allows purification of the protein by $Ni^{2+}$ chelate chromatography. However, a number of other tags is also known and used in the art.

The present invention also provides polynucleotide molecules, including DNA and RNA molecules, that encode the polypeptides disclosed herein. Those skilled in the art will readily recognize that, in view of the degeneracy of the genetic code, considerable sequence variation is possible among these polynucleotide molecules. The polynucleotide may be single or double-stranded. It is to be recognized that according to the present invention, when a polynucleotide is claimed as described herein, it is understood that what is claimed are both the sense strand, the antisense strand and the DNA as double-stranded having both the sense and antisense strand annealed together by their respective hydrogen bonds. Also claimed is the messenger RNA (mRNA) which encodes the polypeptides of the present invention. Messenger RNA will encode a polypeptide using the same codons as those used by DNA, with the exception that each thymine nucleotide (T) is replaced by a uracil nucleotide (U).

Methods for preparing DNA and RNA are well known in the art. A full-length clone encoding Cyp c 1.01 can be obtained by conventional cloning procedures. The DNA encoding Cyp c 1.01 may be amplified by polymerase chain reaction (PCR) employing suitable specific primers. The polynucleotides of the present invention may also be synthesized chemically, for example using the phosphoramidite method. The coding sequence of Cyp c 1.01 cDNA is shown in SEQ ID NO:18.

The invention further relates to a vector or plasmid containing a polynucleotide as described above. In general, the polynucleotide sequence encoding a polypeptide of the invention is operably linked to other genetic elements required for its expression, generally including a transcription promoter and terminator, within an expression vector. The vector will also commonly contain one or more selectable markers (e.g., genes coding for antiviotics resistance) or one or more origins of replication, although those skilled in the art will recognize that within certain systems selectable markers may be provided on separate vectors, and replication of the exogenous DNA may be provided by integration into the host cell genome. Selection of promoters, terminators, selectable markers, vectors and other elements is a matter of routine design within the level of ordinary skill in the art. Many such elements are described in the literature and are available through commercial suppliers.

Another aspect of the invention is a host cell transformed or transfected with a vector or a plasmid according to the invention. The host cells may be prokaryotic or eukaryotic cells. Prokaryotic host cells, including strains of the bacteria *Escherichia coli, Bacillus* and other genera are useful host cells within the present invention. Yeast, insect cells or mammalian cell lines like CHO cells can be used as eukaryotic host cells. Techniques for transforming these hosts and expressing foreign DNA sequences cloned therein are well known in the art (see, e.g., Sambrook et al., Molecular Cloning, a Laboratory Manual, Cold Spring Harbor Laboratory, 1989).

The host cells of the invention may be used to produce the polypeptides of the invention. Yet another aspect of the invention therefore is a method of preparing a polypeptide according to the invention comprising culturing host cells described above under conditions that said polypeptide is expressed and optionally recovering said polypeptide from the host cells. When expressing a polypeptide of the invention in bacteria such as E. coli, the polypeptide may be retained in the cytoplasm, possibly as insoluble inclusion bodies. In this case, the cells are lysed and the inclusion bodies are recovered and denatured using, for example, guanidine isothiocyanate or urea. The denatured polypeptide can then be refolded by diluting the denaturant, such as by dialysis against a solution of urea and a combination of reduced and oxidized glutathione, followed by dialysis against a buffered saline solution.

Transformed or transfected host cells are cultured according to conventional procedures in culture medium containing nutrients and other components required for the growth of the chosen host cells. A variety of suitable media, including defined media and complex media, are known in the art and generally include a carbon source, a nitrogen source and minerals. It is preferred to purify the peptides of the present invention to $\geq 80\%$ purity, more preferably $\geq 95\%$ purity, and particularly preferred is a pharmaceutically pure state that is greater than 99.9% pure with respect to contaminating macromolecules, particularly other proteins and nucleic acids, and free of infectious and pyrogenic agents. Preferably, a purified polypeptide of the invention is substantially free of other polypeptides. Expressed recombinant polypeptide of the invention can be purified using fractionation and/or conventional purification methods and media. Ammonium sulfate precipitation and acid or chaotrop extraction may be used for fractionation of samples. The polypeptides of the invention may also be isolated by affinity chromatography using antibodies directed to the polypeptide. Shorter polypeptides are preferably purified using HPLC. Methods of protein purification are described e.g. in Methods in Enzymology, Volume 182. Guide to Protein Purification. Academic Press New York 1990 and Scopes, Protein Purification. Springer Verlag, Heidelberg 1994.

The polypeptides of the invention may also be prepared through chemical synthesis, for example, as described by Merryfield, J. Am. Chem. Soc. 85:2149, 1963 and Etherton et al., Solid Phase Peptide Synthesis: A Practical Approach, IRL Press, Oxford 1989.

The invention further relates to the use of the polypeptide or polynucleotide or cell of the invention for the manufacture of a medicament for treating and/or preventing an allergic disorder. The disorder usually is an allergy to one or more fish allergens, e.g. to Cyp c 1.01. Preferably, the disorder is IgE-mediated fish hypersensitivity. It has been found that Cyp c 1.01 contains most of the relevant IgE epitopes of different fish allergens. Therefore, the polypeptides or polynucleotides may be used in the treatment of almost any fish allergy. Preferably, the allergic disorder to be treated is allergy to Cyp c 1.01 or to at least one of the proteins listed in table 1 above. The medicament may be used for the therapeutic treatment of an allergic disorder or for prophylactic vaccination to prevent development of the disorder.

The invention also pertains to a pharmaceutical composition comprising at least one polypeptide or at least one polynucleotide of the invention. The composition may further comprise a pharmaceutically acceptable carrier or diluent. Preferably, the polypeptide of the invention has been coupled to a carrier molecule such as KLH.

Another aspect of the invention is a pharmaceutical kit comprising at least one polypeptide or polynucleotide of the invention. The kit may comprise two or more different polypeptides or two or more different polynucleotides according to the present invention. In one embodiment the kit comprises at least one mutated polypeptide derived from Cyp c 1.01 and at least one mutated polypeptide derived from another fish allergen. Other allergens from carp or from other fish and their epitopes may be contained.

For pharmaceutical use, the polypeptides of the present invention are formulated for oral or parenteral, particularly subcutaneous, delivery according to conventional methods. In general, pharmaceutical formulations will include a polypeptide of the invention in combination with a pharmaceutically acceptable vehicle, such as saline, buffered saline, 5% dextrose in water or the like. Formulations may further include one or more excipients, preservatives, solubilizers, buffering agents, albumin to prevent protein loss on vial surfaces, etc. Methods of formulation are well known in the art and are disclosed, for example, in Remington: The Science and Practice of Pharmacy, Gennaro, Ed., Mack Publishing Co., Easton, Pa., 19th Edition 1995. Therapeutic or prophylactic doses will generally be in the range of 0.1-100 µg per injection in a volume of 100-200 µl, with the exact dose determined by the physician according to accepted standards, taking into account the nature and severity of the condition to be treated, patient traits, etc. Determination of dose is within the level of ordinary skill in the art. The amount may vary depending on the mode of treatment. During immunotherapy treatment single doses of about 25 µg to 75 µg can be administered in a volume of about 100 µl per injection. In case of oral administration a dosage of 0.1 µg to 50 mg can be envisaged. In the case of vaccinations, patients are usually not treated several times a day except for "rush immunotherapy". Common immunotherapies include about 8 vaccinations that are administered in intervals of one to two weeks and that are continued over a period of 2 to 3 years. Preferably, 4 injections per year with an interval of 3 months over 3 to 5 years are applied. In a particular embodiment, more than one polypeptide is contained in the pharmaceutical composition.

The polynucleotide of the invention is useful in DNA vaccination to treat and/or prevent an allergic disorder, preferably fish allergy.

The invention also relates to the use of hypoallergenic parvalbumin polypeptides, polynucleotides encoding hypoallergenic polypeptides or cells expressing hypoallergenic parvalbumins for the preparation of a medicament for the treatment of IgE-mediated fish hypersensitivity. Such a medicament may be composed of the polynucleotide, which could be directly used for DNA-based vaccination against fish allergy. Alternatively, the hypoallergenic polypeptide might be used to prepare formulations for oral, sublingual or parenteral treatment of Type I allergic disorders. Modes of application for parenteral treatments may be nasal administration of the hypoallergenic parvalbumin or subcutaneous injection of adjuvant-bound hypoallergenic polypeptides. Furthermore, possible applications comprise also cell-based forms of immunotherapy. In this case antigen presenting cells are transformed with vectors containing the polynucleotide sequence of the hypoallergen and they then express the hypoallergen in vivo.

The invention also relates to the pharmaceutical composition of the medicament containing a polypeptide, polynucleotide or a cell according to the invention. This includes pharmaceutically acceptable carriers or diluents like buffers or salt solutions. In a particular embodiment the pharmaceutical composition also contains an adjuvant.

One or both of the functional calcium-binding sites of rCyp c 1.01 were modified by replacement of two acidic amino acids by non-polar residues. Surprisingly, introduction of such point mutations in only one of the calcium-binding domains displayed already severe effects on the IgE reactivity of the allergen. However, variable changes of IgE-binding capacity were observed, depending on the sera used and some patients even exhibited higher IgE reactivities to such parvalbumin mutants than to the wild-type protein. In contrast, modifications in both of the calcium-binding domains apparently resulted in disruption of all the important IgE epitopes, since IgE reactivity was completely abolished in all sera tested. With a few amino acid changes the inventors thus succeeded to convert a highly reactive food allergen (rCyp c 1.01) into hypoallergenic molecules which can be used for allergen-specific immunotherapy of fish allergy.

In view of the stability of parvalbumin, it could not have been expected that only few point mutations (amino acid substitutions) would be sufficient to produce a polypeptide exhibiting reduced allergenic activity.

The remarkable IgE cross-reactivity among parvalbumins of commonly consumed fish species and the fact that recombinant carp parvalbumin (rCyp c 1.01) contains most of the IgE epitopes present in allergen extracts of several fish species (Swoboda et al., 2002) suggests that rCyp c 1.01-based hypoallergenic molecules can be used to treat the majority of fish allergic patients.

Hypoallergenic parvalbumin molecules will therefore open new avenues for immunotherapy of IgE-mediated fish hypersensitivity. Since the hypoallergenic variants consist of defined components, it will be possible to produce well defined formulations for vaccination treatment. Furthermore, the lack of allergenic activity will allow administration of the hypoallergenic parvalbumins at high doses, comparable to vaccines regularly used for prevention of viral infections, which will result in a high efficacy of the treatment. In this respect it may be considered to use these molecules also for prophylactic vaccination or tolerance induction in not yet sensitised individuals.

The various embodiments of the invention described herein may be cross-combined, in particular the preferred forms of the aspects of the invention.

DESCRIPTION OF THE TABLES AND FIGURES

Table 1. Examples of naturally occurring fish parvalbumins.

Table 2. Percentage inhibition of IgE reactivity to cod, tuna and salmon protein extracts after preabsorption of sera with recombinant carp parvalbumin (as measured in the CAP-FEIA system).

Table 3. IgE reactivity of fish allergic patients to dot-blotted recombinant parvalbumin (wild-type) and to the parvalbumin mutants (Mut-EF, Mut-CD, Mut-CD/EF). IgE reactivity was quantified by gamma counting. Results are displayed in counts per minute (cpm).

FIG. 1: Far-ultraviolet circular dichroism analysis of purified recombinant parvalbumin (Wild-type) and the parvalbumin mutants (Mut-EF, Mut-CD, Mut-CD/EF). Results are expressed as the mean residue ellipticity ($\Theta$) (y-axis) at a given wave length (x-axis).

FIG. 2: SDS-PAGE and immunoblot analysis of purified recombinant parvalbumin (Wild-type) and of the parvalbumin mutants (Mut-EF, Mut-CD, Mut-CD/EF). A, Coomassie brilliant blue-stained SDS-PAGE. B, Immunoblot showing IgE reactivity to the serum of a fish allergic patient. Molecular weights are indicated at the left margins.

Figure 3:
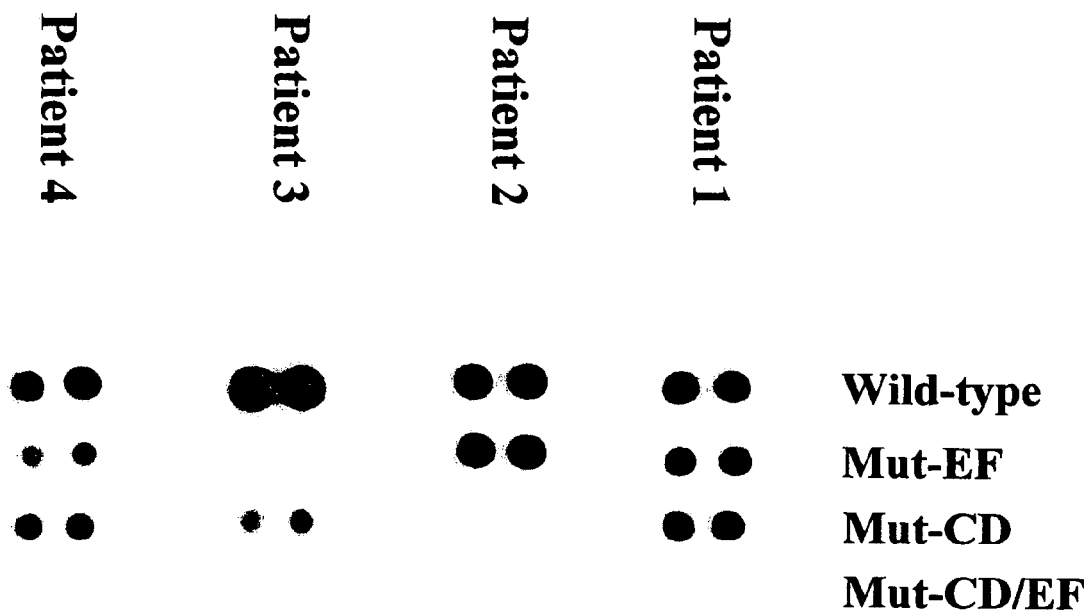

FIG. 3: IgE reactivity of four fish allergic patients to nitrocellulose-dotted duplicates of recombinant parvalbumin (Wild-type) and of the parvalbumin mutants (Mut-EF, Mut-CD, Mut-CD/EF).

Figure 4:

FIG. 4: Inhibition of IgE binding to nitrocellulose-blotted natural carp parvalbumin after preincubation of the serum from a fish allergic patient with recombinant parvalbumin (Wild-type), with the parvalbumin mutants (Mut-EF, Mut-CD, Mut-CD/EF) or with bovine serum albumin (lane BSA). Molecular weights are indicated at the left margin.

Figure 5:
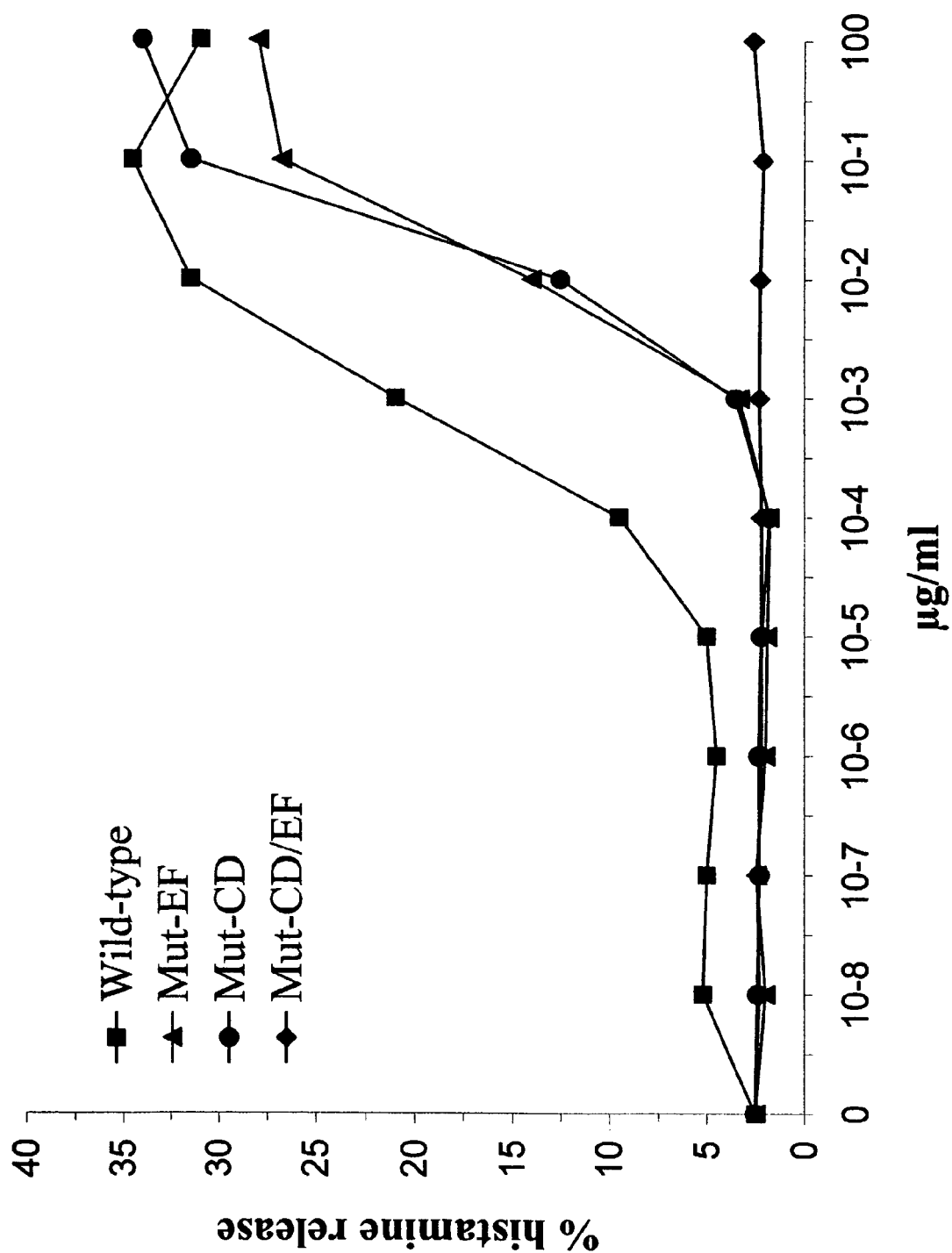

FIG. 5: Biological activity of purified recombinant parvalbumin (Wild-type) and of the parvalbumin mutants (Mut-EF, Mut-CD, MutCD/EF). Induction of histamine release from basophils of a fish allergic patient stimulated by various concentrations (μg/ml) of the recombinant proteins (x-axis). The percentage of histamine released into the supernatant is displayed on the y-axis.

FIG. 6: Alignment of Cyp c 1.01 (SEQ: 1) with amino acid residues 17 to 125 of Ict. Punct. (SEQ ID NO:10). The amino acid residues in the line between the two aligned sequences show where the two sequences are the same.

EXAMPLE 1

Quantitative IgE Inhibition Studies Show that Recombinant Carp Parvalbumin Contains the Majority of IgE Epitopes Present in Various Fish Species To investigate and quantify the cross-reactive potential of recombinant carp parvalbumin, sera from 16 fish-allergic patients were preincubated with recombinant wild-type parvalbumin, expressed and purified as previously described (Swoboda et al., 2002), and then exposed to allergen extracts from cod, tuna, and salmon. Quantification of remaining IgE reactivity by CAP-FEIA measurements revealed a reduction of IgE binding to cod extract ranging between 62% and 96%, to tuna extract between 33% and 98% and to salmon extract between 41% and 95% (Table 2). These findings indicated that recombinant carp parvalbumin represents a highly cross-reactive allergen, which contains a large portion of IgE epitopes present in allergen extracts of various fish species.

Experimental Protocol:

Sera from 16 fish-allergic patients were preincubated with 5 μg recombinant carp parvalbumin or, for control purposes, with 5 μg BSA. Remaining IgE reactivity to cod, tuna and salmon fish extracts was quantified using the CAP-FEIA system (Pharmacia, Uppsala, Sweden). The percentage inhibition of IgE binding to fish extracts after preabsorption to the recombinant allergen was calculated as $((cpm_{BSA} - cpm_{parv})/cpm_{BSA}) \times 100$, where $cpm_{BSA}$ and $cpm_{parv}$ indicate IgE binding after preabsorption with BSA and recombinant carp parvalbumin, respectively.

TABLE 2

Percentage inhibition of IgE reactivity to cod, tuna and salmon extracts after preabsorption of sera with recombinant carp parvalbumin (as measured in the CAP-FEIA System).

| Serum | Cod | Tuna | Salmon |
|---|---|---|---|
| 1 | 62% | 74% | 41% |
| 2 | 87% | 95% | 88% |
| 3 | 96% | 45% | 83% |
| 4 | 83% | 62% | 74% |
| 5 | 64% | 45% | 69% |
| 6 | 90% | 81% | 73% |
| 7 | 69% | 43% | 58% |
| 8 | 66% | 33% | 50% |
| 9 | 85% | 62% | 59% |
| 10 | 85% | 85% | 62% |
| 11 | 85% | 83% | 70% |
| 12 | 82% | 95% | 85% |
| 13 | 91% | 96% | 92% |
| 14 | 95% | 98% | 91% |
| 15 | 88% | 96% | 94% |
| 16 | 68% | 80% | 95% |
| Mean | 76% | 69% | 70% |

EXAMPLE 2

Construction of Parvalbumin Mutants

In order to modify the carp parvalbumin cDNA Cyp c 1.01 (EMBL accession number AJ292211) in one or both of the functional calcium binding sites (CD- or EF domain), site-directed mutagenesis was carried out using the Chameleon Double-Stranded, Site-Directed Mutagenesis Kit (Stratagene, La Jolla, Calif.). The $Ca^{2+}$-binding domains were mutated by replacing the first and third amino acid of the calcium binding loops (Asp) by non-polar Ala residues. Mutagenesis experiments were performed according to the manufacturer's instructions with two synthetic oligonucleotides (mutCD and mutEF) using Cyp c 1.01 DNA cloned into the expression vector pET-17b (Swoboda et al., 2002) as a template. Both oligonucleotides encompassed 45 bp of the parvalbumin cDNA. Primer mutCD (5'-AAG GCC TTT GCT GTC ATT GCC CAA GCC AAG AGC GGC TTC ATT GAG-3', SEQ ID NO:16) introduced changes in codons 52 (GAC→GCC) and 54 (GAC→GCC) and mutEF (5'-GCC TTC CTG AAA GCT GGA GCC TCT GCT GGT GAT GGC AAG ATT GGA-3'; SEQ ID NO:17) in codons 91 (GAC→GCC) and 93 (GAT→GCT), respectively. Modified codons are underlined in the oligonucleotide sequences. Modifications were confirmed by dideoxynucleotide chain-termination sequencing (Sanger et al 1977) using a T7 sequencing kit (Pharmacia, Uppsala, Sweden) and resulting proteins were termed Mut-CD (mutation in CD domain), Mut-EF (mutation in EF domain) and mut-CD/EF (mutated in both domains).

EXAMPLE 3

Figure 2A:
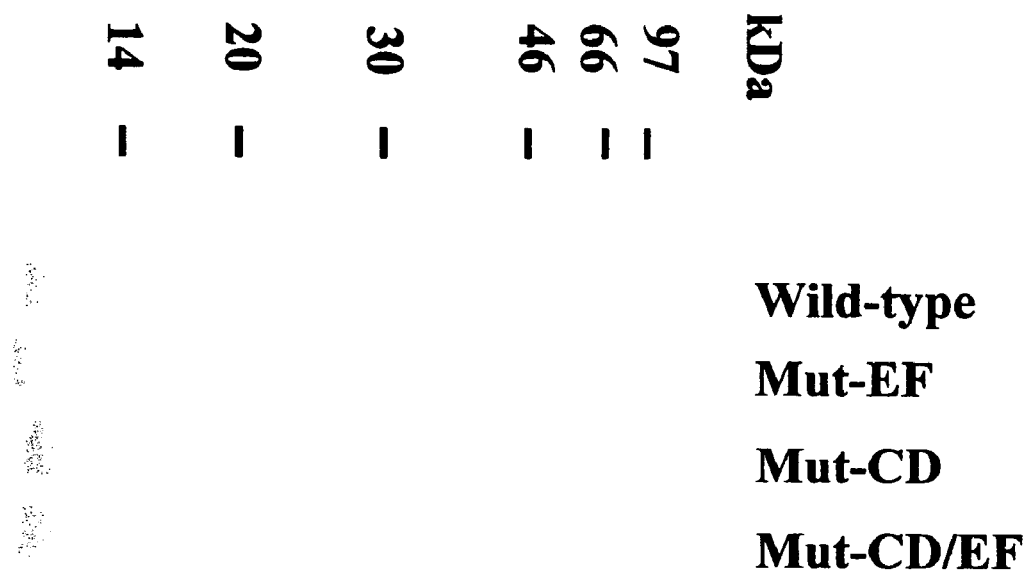
Figure 2B:
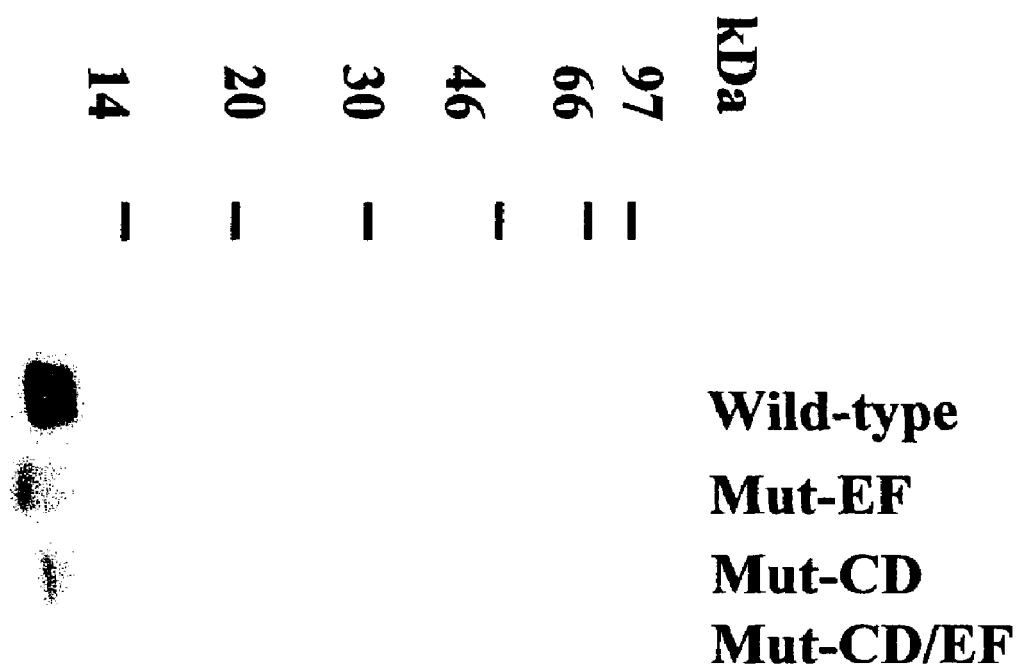

Expression and Purification of Recombinant Carp Parvalbumin and of the Parvalbumin Mutants Recombinant wild-type parvalbumin and the three parvalbumin mutants were expressed in *Escherichia coli* strain BL21(DE3). Isopropylthiogalactopyranoside (IPTG)-induced expression of Mut-CD and Mut-EF proteins resulted in a protein production similar to that observed for the wild-type protein (Swoboda et al., 2002), with 25-30% recombinant protein per total *E. coli* protein. However, bacteria expressing Mut-CD/EF grew more slowly and only approximately 2-3% of total bacterial protein represented Mut-CD/EF protein. Recombinant proteins were purified from the soluble cytoplasmic fractions of bacterial extracts by anion exchange chromatography to about 95% homogeneity as judged by Coomassie brilliant blue staining of 15% sodium dodecyl sulfate polyacrylamid gels (SDS-PAGE; FIG. 2A) (Laemmli 1970).

Experimental Protocol:

Expression of recombinant proteins was induced in *E. coli* BL21(DE3) cells, which had been grown in LB-medium containing 100 mg/l ampicillin to an $OD_{600}$ of 0.4. After an induction of two hours at 37° C. the majority of the protein was found in the soluble fractions of the bacterial extract. Cells were harvested, resuspended in 10 mM Tris (pH 7.5), 1 mM PMSF and lysed by several freeze-thaw cycles with freezing in liquid nitrogen and thawing at 10°-15° C. In case of Mut-CD/EF thawed cells were finally also mechanically disrupted with an ultraturrax (Polytron, Kinematica AG, Switzerland). After centrifugation at 20,000×g for 30 min at 4° C. the cleared supernatant was applied to a DEAE cellulose-Sepharose column (DEAE Sepharose Fast Flow, Pharmacia Biotech, Uppsala, Sweden). Fractions containing the purified proteins were eluted with a linear salt gradient (0-0.5 M NaCl in 10 mM Tris, pH 7.5) and dialysed against PBS (pH 7.4).

EXAMPLE 4

Structural analysis of the parvalbumin mutants shows that Point-Mutations Lead to Significant Conformational Changes The far-ultraviolet CD spectrum (FIG. 1) of the recombinant wild-type parvalbumin was characterised by two broad minima at 208 nm and 223 nm and a strong maximum below 200 nm. Such a shape is typical for a well-structured protein with a considerable amount of α-helices. Overall the spectra of the mutants that had been modified in one of the calcium binding domains (Mut-CD and Mut EF) showed the same characteristics of folded proteins as the wild-type protein. However, mutations introduced in both calcium binding domains (as in Mut-CD/EF) led to remarkable differences in the shape of the far-UV spectrum. The observed single broad minimum at about 202 nm indicates a significant decrease in the α-helical content and in the secondary structure of the molecule and a transition into a random coiled, unfolded conformation. By introduction of a few targeted point mutations the inventors had thus succeeded to significantly modify the structure of this highly stable allergen.

Experimental Protocol:

Circular dichroism (CD) measurements were performed on a Jasco (Tokyo, Japan) J-715 spectropolarimeter with protein concentrations between 12.3-24.0 μM using a 1 mm path-length quartz cuvette (Hellma, Mullheim, Baden, Germany) equilibrated at 20° C. Spectra were recorded with 0.2 nm resolution at a scan speed of 50 nm/min and resulted from averaging of 3 scans. The final spectra were corrected by subtracting the corresponding baseline spectrum obtained under identical conditions. Results are expressed as the mean residue ellipticity (Θ) at a given wavelength.

EXAMPLE 5

Parvalbumin Mutants Show Reduced IgE Binding Capacity

The IgE reactivity to recombinant wild-type and mutated parvalbumins was analysed in immunoblot and dot blot experiments. The immunoblot shown in FIG. 2B was probed with the serum of a fish allergic patient and exemplifies the IgE binding capacity of the denatured, immobilized proteins. Sera always displayed strong IgE reactivity towards the wild-type allergen, reduced IgE binding to Mut-CD or Mut-EF and no binding to Mut-CD/EF.

Furthermore, the inventors also evaluated the IgE binding capacity of the non-denatured, dot-blotted parvalbumin proteins using sera from 23 fish allergic patients (FIG. 3). Dot blot assays confirmed the data obtained in the immunoblot experiments and showed that modifications in one of the calcium binding domains (Mut-CD or Mut-EF) resulted in variable changes of IgE reactivity depending on the sera used. Some patients even displayed higher IgE reactivities to Mut-CD or Mut-EF than to the wild-type allergen. Mutations in both calcium-binding regions (Mut-CD/EF), on the other hand, caused a complete loss of IgE binding capacity in all of the sera tested. In case of Mut-CD/EF, quantification of the IgE reactivity by gamma counting revealed IgE binding capacities between 0.5% to 67.6% of the IgE binding capacities of parvalbumin wild-type protein (Table 3).

TABLE 3

IgE reactivity of fish allergic patients to dot-blotted recombinant parvalbumin and to the parvalbumin mutants. IgE reactivity was quantified by gamma counting. Results are displayed in counts per minute (cpm).

| Patient | Wild-type | Mut-EF | Mut-CD | Mut-CD/EF |
|---|---|---|---|---|
| 1 | 65.9 | 61.6 | 8.6 | 2.6 |
| 2 | 16.2 | 33.3 | 13.7 | 8.6 |
| 3 | 82.5 | 85.5 | 26.0 | 0.6 |
| 4 | 28.9 | 106.0 | 21.9 | 8.6 |
| 5 | 62.0 | 31.3 | 47.5 | 9.6 |
| 6 | 92.2 | 23.2 | 26.0 | 24.5 |
| 7 | 33.7 | 29.3 | 14.8 | 4.6 |
| 8 | 72.7 | 60.6 | 87.5 | 4.6 |
| 9 | 329.2 | 193.9 | 128.4 | 1.6 |
| 10 | 194.6 | 104.0 | 48.5 | 12.6 |
| 11 | 438.4 | 374.6 | 113.1 | 1.4 |
| 12 | 75.7 | 138.3 | 21.9 | 1.6 |
| 13 | 258.0 | 206.0 | 110.0 | 4.6 |
| 14 | 172.2 | 62.6 | 12.7 | 12.6 |
| 15 | 192.7 | 344.3 | 60.8 | 5.6 |
| 16 | 211.2 | 75.7 | 131.5 | 6.6 |
| 17 | 751.8 | 882.1 | 123.5 | 10.8 |
| 18 | 738.2 | 464.0 | 496.0 | 46.6 |
| 19 | 1442.8 | 45.2 | 165.2 | 17.1 |
| 20 | 473.4 | 169.6 | 208.1 | 19.0 |
| 21 | 84.8 | 89.4 | 70.1 | 41.5 |

The inventors also investigated the capacity of the recombinant parvalbumin variants to inhibit IgE binding to nitrocellulose-blotted natural carp parvalbumin using immunoblot competition assays (FIG. 4). In these experiments patients sera were preadsorbed to an excess of the wild-type or the mutant proteins before exposure to the immobilised natural allergen. During preincubation reaction between proteins and IgE antibodies thus occurred in solution and thereby mimicked the in vivo situation. As shown in FIG. 4 IgE binding to the natural allergen was completely inhibited by addition of recombinant wild-type protein. Mut-CD and Mut-EF exhibited a markedly lower inhibition capacity than the wild-type protein, whereas preincubation with Mut-CD/EF had no effect on the IgE binding to natural parvalbumin.

These results suggested that by amino acid substitutions in either of the calcium binding sites the overall structure of the parvalbumin molecule was not significantly altered. Nevertheless, it can also be concluded that mutations in one of the domains did have an effect on local B cell epitopes, because Mut-CD or Mut-EF caused remarkable reduction of IgE reactivity in some of the sera. However, modifications in both calcium binding regions caused such a significant change of conformational epitopes and/or unfolding of the protein that IgE binding was completely abolished in all of the allergic patients sera tested.

Experimental Protocols:

Immunoblot and Dot Blot Analysis:

Reactivities of recombinant carp parvalbumin variants to serum IgE from fish allergic patients were determined in immunoblot or dot blot experiments. For immunoblots, 1.5 µg of the purified proteins were separated by SDS-PAGE (Laemmli 1970) and blotted onto nitrocellulose membranes (Schleicher & Schuell, Dassel, Germany; Towbin et al., 1979). For dot blot analysis, aliquots of approximately 0.5 µg of the parvalbumin proteins were dotted on nitrocellulose membranes (Schleicher & Schuell). In both cases filters were probed with patients sera diluted 1:10 in PBST (PBS, pH 7.5, containing 0.5% v/v Tween 20) and bound IgE antibodies were detected with 1:15 diluted $^{125}$I-labelled anti-human IgE antibodies (RAST, Pharmacia, Uppsala, Sweden).

Immunoblot Competition Experiments:

For immunoblot inhibition experiments, sera from fish-allergic patients were preincubated with purified recombinant proteins and, for control purposes, with an immunologically unrelated protein (BSA) (10 µg/ml of 1:10 diluted serum). Thereafter, nitrocellulose-blotted purified natural parvalbumin was incubated with the preadsorbed serum samples and bound IgE was detected using $^{125}$I-rabbit anti-human IgE (Pharmacia).

EXAMPLE 6

Reduced ability of Recombinant Parvalbumin Mutants to Induce Basophil Histamine Release To analyse the biological activity of the parvalbumin mutants, peripheral blood basophils of a fish allergic patient were incubated with different concentrations of the recombinant wild-type and mutant proteins (FIG. 5). A strong dose-dependent release of histamine from the basophil granulocytes was induced by the recombinant wild-type protein. Amounts of released histamine were less, if granulocytes were exposed to Mut-CD or Mut-EF and highly reduced after exposure of the cells to Mut-CD/EF. This significantly reduced allergenic activity of Mut-CD/EF suggests that the mutated parvalbumin derivative represents a suitable candidate molecule for therapeutic applications.

Experimental Protocol:

Basophil Histamine Release Assay:

Granulocytes were isolated from heparinised blood samples of a fish allergic patient by dextran sedimentation. Cells were incubated with increasing concentrations of recombinant carp parvalbumin variants, anti-human IgE antibody, or buffer as previously described (Valent et al., 1989). Liberated histamine was measured in the cell-free supernatants by radioimmunoassay (Immunotech, Marseille, France).

REFERENCES

Aas, K. 1987. Fish allergy and the cod allergen model. In *Food allergy and intolerance*, J. Brostoff, and S. T. Challacombe, eds. Balliere Tindall, London, p. 356.

Aas, K., and S. M. Elsayed. 1969. Characterisation of a major allergen (cod). *J. Allergy* 44:333.

Berchtold, M. W. 1989. Structure and expression of genes encoding three-domain $Ca^{2+}$-binding proteins parvalbumin and oncomodulin. *Biochim. Biophys. Acta* 1009:201.

Bischoff, S. C., A. Herrmann, and M. P. Manns. 1996. Prevalence of adverse reactions to food in patients with gastrointestinal diseases. *Allergy* 51:811.

Bousquet, J., R. Lockey, H. J. Malling, and the WHO panel members. 1998. Allergen immunotherapy: therapeutic vaccines for allergic diseases. *J. Allergy Clin. Immunol.* 102:558.

Bugajsaka-Schretter, A., L. Elfman, T. Fuchs, S. Kapiotis, H. Rumpold, R. Valenta, and S. Spitzauer. 1998. Parvalbumin, a cross-reactive fish allergen, contains IgE-binding epitopes sensitive to periodate treatment and $Ca^{2+}$ depletion. *J. Allergy Clin. Immunol.* 101:67.

Bugajska-Schretter, A., M. Grote, L. Vangelista, P. Valent, W. R. Sperr, H. Rumpold, A. Pastore, R. Reichelt, R. Valenta, and S. Spitzauer. 2000. Purification, biochemical, and immunological characterisation of a major food allergen: different immunoglobulin E recognition of the apo- and calcium-bound forms of carp parvalbumin. *Gut.* 46:661.

De Martino, M., E. Novembre, L. Galli, A. De Marco, P. Botarelli, E. Marano, and A. Vierucci. 1990. Allergy to different fish species in cod-allergic children: in vivo and in vitro studies. *J. Allergy Clin. Immunol.* 86:909.

Declercq, J. P., B. Tinant, J. Parello, and J. Rambaud. 1991. Ionic interactions with parvalbumins. Crystal structure determination of pike 4.10 parvalbumin in four different ionic environments. *J. Mol. Biol.* 220:1017.

Etesamifar, M., and B. Wüthrich. 1998. IgE-mediated food allergies including oral allergy syndrome in 383 patients. *Allergologie* 21:451.

Elsayed, S., and K. Aas. 1971. Characterisation of a major allergen (cod). Observation on effect of denaturation on the allergenic activity. *J. Allergy* 47:283.

Etherton et al., *Solid Phase Peptide Synthesis: A Practical Approach*, IRL Press, Oxford 1989.

Goodman, M., and J. F. Pechere. 1977. The evolution of muscular parvalbumins investigated by the maximum parsimony method. *J. Mol. Evol.* 9:131.

Heizmann, C. W., and W. Hunziker. 1991. Intracellular calcium-binding proteins: more sites than insights. *Trends Biochem. Sci.* 16:98.

Ikura, M. 1996. Calcium-binding and conformation response in EF-hand proteins. *Trends Biochem. Sci.* 21:14.

Kretsinger, R. H., and C. E. Nockold. 1973. Carp muscle calcium-binding protein. II. Structure determination and general description. *J. Biol. Chem.* 248:3313.

Kretsinger, R. H. 1980. Structure and evolution of calcium-modulated proteins. *C. R. C. Crit. Rev. Biochem.* 8:119.

Laemmli, U.K. 1970. Cleavage of the structural proteins during the assembly of the head of bacteriophage T4. *Nature* 227:680.

Lehky, P., H. E. Blum, E. A. Stein, and E. H. Fisher. 1974. Isolation and characterisation of parvalbumins from skeletal muscle of higher vertebrates. *J. Biol. Chem.* 249:4332.

Lindstroem, C. D. V., T. van Do, I. Hordvik, C. Endresen, and S. Elsayed. 1996. Cloning of two distinct cDNAs encoding parvalbumin, the major allergen of Atlantic salmon (Salmo salar). *Scand. J. Immunol.* 44:335.

Merrifield et al. 1963. *J. Am. Chem. Soc.* 85:2149.

Niederberger et al. 1998. *J. Allergy Clin. Immunol.* 102:579.

O'Neil, C., A. A. Helbling, and S. B. Lehrer. 1993. Allergic reactions to fish. *Clin. Rev. Allergy* 11:183.

Pascual, C., M. M. Esteban, and J. F. Crespo. 1992. Fish allergy: evaluation of the importance of cross-reactivity. *J. Pediatr.* 121:29.

Pauli et al. 2000. *Clin. Exp. Allergy* 30:1076.

Pechere, J. F. 1997. The significance of parvalbumin among muscular calcium proteins. In *Calcium-Binding Proteins and Calcium*. R. H. Wasserman, R. Corradino, E. Carafoli, R. H. Kretsinger, D. H. MacLennan, and F. L. Siegel, eds. Elsevier, Holland, p. 213.

Permyakov, E. A., V. N. Medvedkin, Y. V. Mitin, and R. H. Kretsinger. 1991. Noncovalent complex between domain AB and domain CD*EF of parvalbumn. *Biochim. Biiophys. Acta* 1076:667.

Remington: *The Science and Practice of Pharmacy*, Gennaro, Ed., Mack Publishing Co., Easton, Pa., 19th Edition 1995.

Sambrook et al., *Molecular Cloning, a Laboratory Manual*, Cold Spring Harbor Laboratory, 1989.

Sampson, H. 1999. Food allergy. Part 1: Immunopathogenesis and clinical disorders. *J. Allergy Clin. Immunol.* 103: 717.

Sanger, F., S. Nicklen, and A. R. Coulson. 1977. DNA sequencing with chain terminating. *Proc. Natl. Acad. Sci. USA* 74:5463.

Scopes, *Protein Purification*. Springer Verlag, Heidelberg 1994.

Swoboda, I., A. Bugajska-Schretter, P. Verdino, W. Keller, W. R. Sperr, P. Valent, R. Valenta, and S. Spitzauer. 2002. Recombinant carp parvalbumin, the major cross-reactive fish allergen: A tool for diagnosis and therapy of fish allergy. *J. Immunol.* 168:4576.

Tatusova et al. 1999. *FEMS Microbiol. Lett.* 174:247.

Towbin, H., T. Staehelin, and J. Gordon. 1979. Electrophoretic transfer of proteins from polyacrylamide gels to nitrocellulose sheets: procedure and some applications. *Proc. Natl. Acad. Sci. USA* 76:4350.

Valent, P., J. Besemer, M. Muhm, O. Majdic, K. Lechner, and P. Bettelheim. 1989. Interleukin 3 activates human blood basophils via high-affinity binding sites. *Proc. Natl. Acad. Sci. USA* 86:5542.

Valenta, R., and D. Kraft. 1995. Recombinant allergens for diagnosis and therapy of allergic diseases. *Curr. Opin. Immunol.* 7:751.

Valenta, R., S. Vrtala, S. Laffer, S. Spitzauer, and D. Kraft. 1998. Recombinant allergens. *Allergy* 53:552.

van Hage-Hamsten et al. 1999. *J. Allergy Clin. Immunol.* 104:969.

Vrtala et al. 1997. *J. Clin. Invest.* 99:1673.

Methods in Enzymology, Vol. 182, *Guide to Protein Purification*, Academic Press New York, 1990.

The invention claimed is:

1. An isolated polypeptide variant of SEQ ID NO: 1, wherein the isolated polypeptide variant comprises the amino acid sequence of SEQ ID NO: 1, except amino acid residues 52, 54, 91 and 93 of SEQ ID NO: 1 are substituted with another amino acid, and wherein the isolated polypeptide variant has less allergenic activity compared to SEQ ID NO: 1.

2. The polypeptide according to claim 1 which is capable of inducing an IgG response against SEQ ID NO: 1 in a mammal.

3. The polypeptide according to claim 1 which induces a histamine release which is reduced compared with SEQ ID NO: 1.

4. The polypeptide according to claim 1 wherein the polypeptide has reduced IgE binding activity compared to SEQ ID NO: 1.

* * * * *

SEQUENCE LISTING

<160> NUMBER OF SEQ ID NOS: 18

<210> SEQ ID NO 1
<211> LENGTH: 109
<212> TYPE: PRT
<213> ORGANISM: Cyprinus carpio

<400> SEQUENCE: 1

Met Ala Phe Ala Gly Ile Leu Asn Asp Ala Asp Ile Thr Ala Ala Leu
1               5                   10                  15

Gln Gly Cys Gln Ala Ala Asp Ser Phe Asp Tyr Lys Ser Phe Phe Ala
            20                  25                  30

Lys Val Gly Leu Ser Ala Lys Thr Pro Asp Asp Ile Lys Lys Ala Phe
        35                  40                  45

Ala Val Ile Asp Gln Asp Lys Ser Gly Phe Ile Glu Glu Asp Glu Leu
    50                  55                  60

Lys Leu Phe Leu Gln Asn Phe Ser Ala Gly Ala Arg Ala Leu Thr Asp
65                  70                  75                  80

Ala Glu Thr Lys Ala Phe Leu Lys Ala Gly Asp Ser Asp Gly Asp Gly
                85                  90                  95

Lys Ile Gly Val Asp Glu Phe Ala Ala Leu Val Lys Ala
            100                 105

<210> SEQ ID NO 2
<211> LENGTH: 109
<212> TYPE: PRT
<213> ORGANISM: Artificial Sequence
<220> FEATURE:
<223> OTHER INFORMATION: D52A, D54A

<400> SEQUENCE: 2

Met Ala Phe Ala Gly Ile Leu Asn Asp Ala Asp Ile Thr Ala Ala Leu
1               5                   10                  15

Gln Gly Cys Gln Ala Ala Asp Ser Phe Asp Tyr Lys Ser Phe Phe Ala
            20                  25                  30

Lys Val Gly Leu Ser Ala Lys Thr Pro Asp Asp Ile Lys Lys Ala Phe
        35                  40                  45

Ala Val Ile Ala Gln Ala Lys Ser Gly Phe Ile Glu Glu Asp Glu Leu
    50                  55                  60

Lys Leu Phe Leu Gln Asn Phe Ser Ala Gly Ala Arg Ala Leu Thr Asp
65                  70                  75                  80

Ala Glu Thr Lys Ala Phe Leu Lys Ala Gly Asp Ser Asp Gly Asp Gly
                85                  90                  95

Lys Ile Gly Val Asp Glu Phe Ala Ala Leu Val Lys Ala
            100                 105

<210> SEQ ID NO 3
<211> LENGTH: 109
<212> TYPE: PRT
<213> ORGANISM: Artificial Sequence
<220> FEATURE:
<223> OTHER INFORMATION: D91A, D93A

<400> SEQUENCE: 3

Met Ala Phe Ala Gly Ile Leu Asn Asp Ala Asp Ile Thr Ala Ala Leu
1               5                   10                  15

Gln Gly Cys Gln Ala Ala Asp Ser Phe Asp Tyr Lys Ser Phe Phe Ala
            20                  25                  30

```
Lys Val Gly Leu Ser Ala Lys Thr Pro Asp Asp Ile Lys Lys Ala Phe
             35                  40                  45

Ala Val Ile Asp Gln Asp Lys Ser Gly Phe Ile Glu Glu Asp Glu Leu
         50                  55                  60

Lys Leu Phe Leu Gln Asn Phe Ser Ala Gly Ala Arg Ala Leu Thr Asp
 65                  70                  75                  80

Ala Glu Thr Lys Ala Phe Leu Lys Ala Gly Ala Ser Ala Gly Asp Gly
                 85                  90                  95

Lys Ile Gly Val Asp Glu Phe Ala Ala Leu Val Lys Ala
             100                 105
```

<210> SEQ ID NO 4
<211> LENGTH: 109
<212> TYPE: PRT
<213> ORGANISM: Artificial Sequence
<220> FEATURE:
<223> OTHER INFORMATION: D52A, D54A, D91A, D93A

<400> SEQUENCE: 4

```
Met Ala Phe Ala Gly Ile Leu Asn Asp Ala Asp Ile Thr Ala Ala Leu
 1               5                  10                  15

Gln Gly Cys Gln Ala Ala Asp Ser Phe Asp Tyr Lys Ser Phe Phe Ala
             20                  25                  30

Lys Val Gly Leu Ser Ala Lys Thr Pro Asp Asp Ile Lys Lys Ala Phe
             35                  40                  45

Ala Val Ile Ala Gln Ala Lys Ser Gly Phe Ile Glu Glu Asp Glu Leu
         50                  55                  60

Lys Leu Phe Leu Gln Asn Phe Ser Ala Gly Ala Arg Ala Leu Thr Asp
 65                  70                  75                  80

Ala Glu Thr Lys Ala Phe Leu Lys Ala Gly Ala Ser Ala Gly Asp Gly
                 85                  90                  95

Lys Ile Gly Val Asp Glu Phe Ala Ala Leu Val Lys Ala
             100                 105
```

<210> SEQ ID NO 5
<211> LENGTH: 62
<212> TYPE: PRT
<213> ORGANISM: Artificial Sequence
<220> FEATURE:
<223> OTHER INFORMATION: EF hand 1

<400> SEQUENCE: 5

```
Ala Phe Ala Gly Ile Leu Asn Asp Ala Asp Ile Thr Ala Ala Leu Gln
 1               5                  10                  15

Gly Cys Gln Ala Ala Asp Ser Phe Asp Tyr Lys Ser Phe Phe Ala Lys
             20                  25                  30

Val Gly Leu Ser Ala Lys Thr Pro Asp Asp Ile Lys Lys Ala Phe Ala
             35                  40                  45

Val Ile Asp Gln Asp Lys Ser Gly Phe Ile Glu Glu Asp Glu
         50                  55                  60
```

<210> SEQ ID NO 6
<211> LENGTH: 19
<212> TYPE: PRT
<213> ORGANISM: Artificial Sequence
<220> FEATURE:
<223> OTHER INFORMATION: EF hand 2

<400> SEQUENCE: 6

-continued

Asp Ser Asp Gly Asp Gly Lys Ile Gly Val Asp Glu Phe Ala Ala Leu
1               5                   10                  15

Val Lys Ala

<210> SEQ ID NO 7
<211> LENGTH: 109
<212> TYPE: PRT
<213> ORGANISM: Danio rerio

<400> SEQUENCE: 7

Met Ala Phe Ala Gly Ile Leu Asn Glu Ala Asp Ile Thr Ala Ala Leu
1               5                   10                  15

Gln Ala Cys Gln Ala Ala Asp Ser Phe Asp Tyr Lys Ser Phe Phe Ala
            20                  25                  30

Lys Val Gly Leu Ser Ala Lys Thr Pro Asp Asp Ile Lys Ala Phe
        35                  40                  45

Ala Val Ile Asp Gln Asp Lys Ser Gly Phe Ile Glu Glu Asp Glu Leu
    50                  55                  60

Lys Leu Phe Leu Gln Asn Phe Ser Ala Gly Ala Arg Ala Leu Thr Asp
65                  70                  75                  80

Ala Glu Thr Lys Ala Phe Leu Lys Ala Gly Asp Ser Asp Gly Asp Gly
                85                  90                  95

Lys Ile Gly Val Asp Glu Phe Ala Ser Leu Val Lys Ala
            100                 105

<210> SEQ ID NO 8
<211> LENGTH: 108
<212> TYPE: PRT
<213> ORGANISM: Cyprinus carpio
<220> FEATURE:
<221> NAME/KEY: MISC_FEATURE
<222> LOCATION: (19)..(19)
<223> OTHER INFORMATION: Xaa is unknown
<220> FEATURE:
<221> NAME/KEY: MISC_FEATURE
<222> LOCATION: (21)..(21)
<223> OTHER INFORMATION: Xaa is unknown

<400> SEQUENCE: 8

Ala Tyr Gly Gly Ile Leu Asn Asp Ala Asp Ile Thr Ala Ala Leu Glu
1               5                   10                  15

Ala Cys Xaa Ala Xaa Asp Ser Phe Asn Ala Lys Ser Phe Phe Ala Lys
            20                  25                  30

Val Gly Leu Ser Ala Lys Thr Pro Asp Asp Ile Lys Lys Ala Phe Ala
        35                  40                  45

Val Ile Asp Gln Asp Lys Ser Gly Phe Ile Glu Glu Asp Glu Leu Lys
    50                  55                  60

Leu Phe Leu Gln Asn Phe Ser Ala Gly Ala Arg Ala Leu Thr Asp Ala
65                  70                  75                  80

Glu Thr Lys Ala Phe Leu Lys Ala Gly Asp Ser Asp Gly Asp Gly Lys
                85                  90                  95

Ile Gly Val Asp Glu Phe Ala Ala Leu Val Lys Ala
            100                 105

<210> SEQ ID NO 9
<211> LENGTH: 109
<212> TYPE: PRT
<213> ORGANISM: Cyprinus carpio

<400> SEQUENCE: 9

```
Met Ala Phe Ala Gly Val Leu Asn Asp Ala Asp Ile Thr Ala Ala Leu
1               5                   10                  15

Glu Ala Cys Lys Ala Ala Asp Ser Phe Asn His Lys Thr Phe Phe Ala
            20                  25                  30

Lys Val Gly Leu Thr Ser Lys Ser Ala Asp Asp Val Lys Lys Ala Phe
                35                  40                  45

Ala Ile Ile Asp Gln Asp Lys Ser Gly Phe Ile Glu Glu Asp Glu Leu
50                  55                  60

Lys Leu Phe Leu Gln Asn Phe Lys Ala Gly Ala Arg Ala Leu Thr Asp
65                  70                  75                  80

Gly Glu Thr Lys Thr Phe Leu Lys Ala Gly Asp Ser Asp Gly Asp Gly
                85                  90                  95

Lys Ile Gly Val Asp Glu Phe Thr Ala Leu Val Lys Ala
            100                 105
```

<210> SEQ ID NO 10
<211> LENGTH: 125
<212> TYPE: PRT
<213> ORGANISM: Ictalurus punctatus

<400> SEQUENCE: 10

```
Val Phe Glu Asn Leu Gln Leu Thr Thr Lys Lys Thr Lys Glu Leu Lys
1               5                   10                  15

Met Ala Phe Ala Gly Val Leu Asn Asp Ala Asp Ile Thr Ala Ala Leu
                20                  25                  30

Asp Ala Cys Lys Ala Asp Gly Ser Phe Asn His Lys Ser Phe Phe Thr
            35                  40                  45

Lys Val Gly Leu Thr Gly Lys Ser Ala Asp Asp Val Lys Lys Ala Phe
50                  55                  60

Ala Ile Ile Asp Gln Asp Lys Ser Gly Phe Ile Glu Glu Asp Glu Leu
65                  70                  75                  80

Lys Leu Phe Leu Gln Asn Phe Lys Ser Ser Ala Arg Ala Leu Thr Asp
                85                  90                  95

Ala Glu Thr Lys Thr Phe Leu Lys Ala Gly Asp Thr Asp Gly Asp Gly
                100                 105                 110

Lys Ile Gly Val Asp Glu Phe Ala Ser Leu Val Lys Ala
            115                 120                 125
```

<210> SEQ ID NO 11
<211> LENGTH: 109
<212> TYPE: PRT
<213> ORGANISM: Gadus morhua

<400> SEQUENCE: 11

```
Met Ala Phe Ala Gly Ile Leu Asn Asp Ala Asp Ile Thr Ala Ala Leu
1               5                   10                  15

Ala Ala Cys Lys Ala Glu Gly Ser Phe Asp His Lys Ala Phe Phe Thr
            20                  25                  30

Lys Val Gly Leu Ala Ala Lys Ser Pro Ala Asp Ile Lys Lys Val Phe
                35                  40                  45

Glu Ile Ile Asp Gln Asp Lys Ser Asp Phe Val Glu Glu Asp Glu Leu
50                  55                  60

Lys Leu Phe Leu Gln Asn Phe Ser Ala Gly Ala Arg Ala Leu Ser Asp
65                  70                  75                  80

Ala Glu Thr Lys Val Phe Leu Lys Ala Gly Asp Ser Asp Gly Asp Gly
                85                  90                  95
```

```
Lys Ile Gly Val Asp Glu Phe Gly Ala Met Ile Lys Ala
            100                 105
```

```
<210> SEQ ID NO 12
<211> LENGTH: 109
<212> TYPE: PRT
<213> ORGANISM: Danio rerio

<400> SEQUENCE: 12

Met Ala Phe Ala Gly Ile Leu Lys Asp Glu Asp Val Ala Ala Leu
1               5                   10                  15

Lys Asp Cys Ala Ala Asp Ser Phe Asn Tyr Lys Asn Phe Phe Ala
                20                  25                  30

Lys Val Gly Leu Ser Ala Lys Ser Pro Asp Asp Ile Lys Lys Ala Phe
            35                  40                  45

Phe Val Ile Asp Gln Asp Lys Ser Gly Phe Ile Glu Glu Asp Glu Leu
    50                  55                  60

Lys Leu Phe Leu Gln Asn Phe Ser Ala Gly Ala Arg Ala Leu Thr Asp
65                  70                  75                  80

Ala Glu Thr Lys Ala Phe Leu Ser Ala Gly Asp Ser Asp Gly Asp Gly
                85                  90                  95

Lys Ile Gly Val Asp Glu Phe Ala Leu Leu Val Lys Ala
            100                 105
```

```
<210> SEQ ID NO 13
<211> LENGTH: 109
<212> TYPE: PRT
<213> ORGANISM: Danio rerio

<400> SEQUENCE: 13

Met Ala Phe Ala Gly Val Leu Asn Asp Ala Asp Ile Ser Ala Ala Leu
1               5                   10                  15

Glu Ala Cys Lys Ala Ala Asp Ser Phe Asn His Lys Ser Phe Phe Ala
                20                  25                  30

Lys Val Gly Leu Ala Ser Lys Ser Ala Asp Glu Val Lys Lys Ala Phe
            35                  40                  45

Ala Ile Ile Asp Gln Asp Lys Ser Gly Phe Ile Glu Glu Glu Glu Leu
    50                  55                  60

Lys Leu Phe Leu Gln Asn Phe Lys Ala Asp Ala Arg Ala Leu Thr Asp
65                  70                  75                  80

Gly Glu Thr Lys Thr Phe Leu Lys Ala Gly Asp Ser Tyr Gly Asp Gly
                85                  90                  95

Lys Ile Gly Ile Tyr Glu Phe Ala Ala Phe Val Lys Ala
            100                 105
```

```
<210> SEQ ID NO 14
<211> LENGTH: 108
<212> TYPE: PRT
<213> ORGANISM: Electrophorus electricus

<400> SEQUENCE: 14

Ala Phe Ala Gly Val Leu Asn Asp Ala Asp Ile Thr Ala Ala Leu Asp
1               5                   10                  15

Ala Cys Lys Ala Asp Gly Ser Phe Asp His Lys Ala Phe Phe Glu Lys
                20                  25                  30

Val Gly Leu Thr Ser Lys Ser Ala Asp Asp Val Lys Lys Ala Phe Ala
            35                  40                  45

Ile Ile Asp Gln Asp Lys Ser Gly Phe Ile Glu Glu Asp Glu Leu Lys
```

```
                     50                  55                  60
Leu Phe Leu Gln Asn Phe Lys Ser Gly Ala Arg Ala Leu Thr Asp Ala
 65                  70                  75                  80

Glu Thr Lys Ala Phe Met Lys Ala Gly Asp Thr Asp Gly Asp Gly Lys
                 85                  90                  95

Ile Gly Val Glu Glu Phe Ser Ala Leu Val Lys Ala
                100                 105

<210> SEQ ID NO 15
<211> LENGTH: 109
<212> TYPE: PRT
<213> ORGANISM: Scomber japonicus

<400> SEQUENCE: 15

Met Ala Phe Ala Ser Val Leu Lys Asp Ala Glu Val Thr Ala Ala Leu
 1               5                  10                  15

Asp Gly Cys Lys Ala Ala Gly Ser Phe Asp His Lys Lys Phe Phe Lys
                20                  25                  30

Ala Cys Gly Leu Ser Gly Lys Ser Thr Asp Glu Val Lys Lys Ala Phe
            35                  40                  45

Ala Ile Ile Asp Gln Asp Lys Ser Gly Phe Ile Glu Glu Glu Glu Leu
        50                  55                  60

Lys Leu Phe Leu Gln Asn Phe Lys Ala Gly Ala Arg Ala Leu Ser Asp
 65                  70                  75                  80

Ala Glu Thr Lys Ala Phe Leu Lys Ala Gly Asp Ser Asp Gly Asp Gly
                 85                  90                  95

Lys Ile Gly Ile Asp Glu Phe Ala Ala Met Ile Lys Gly
                100                 105

<210> SEQ ID NO 16
<211> LENGTH: 45
<212> TYPE: DNA
<213> ORGANISM: Artificial Sequence
<220> FEATURE:
<223> OTHER INFORMATION: Primer mut CD

<400> SEQUENCE: 16
aaggcctttg ctgtcattgc ccaagccaag agcggcttca ttgag          45

<210> SEQ ID NO 17
<211> LENGTH: 45
<212> TYPE: DNA
<213> ORGANISM: Artificial Sequence
<220> FEATURE:
<223> OTHER INFORMATION: Primer mutEF

<400> SEQUENCE: 17
gccttcctga agctggagc tctgctggt gatggcaaga ttgga           45

<210> SEQ ID NO 18
<211> LENGTH: 330
<212> TYPE: DNA
<213> ORGANISM: Cyprinus carpio

<400> SEQUENCE: 18
atggcattcg ctggaattct gaatgatgct gacatcactg cagccctgca gggctgccaa      60
gctgctgact ccttcgacta caagagcttc ttcgccaagg ttggtctgtc tgccaagact     120
cctgatgaca tcaagaaggc ctttgctgtc attgaccaag acaagagcgg cttcattgag     180
gaggatgagc tgaaactgtt cctgcagaac ttctctgctg cgccagggc actcactgat     240
```

```
gcagagacaa aggccttcct gaaagctgga gactctgatg gtgatggcaa gattggagtt        300
gatgagtttg ctgccctggt caaggcataa                                         330
```